United States Patent
Kärki et al.

(10) Patent No.: US 10,261,015 B2
(45) Date of Patent: Apr. 16, 2019

(54) METHOD AND MEASUREMENT APPARATUS FOR MEASURING SUSPENSION

(71) Applicant: VALMET AUTOMATION OY, Espoo (FI)

(72) Inventors: Pasi Kärki, Kajaani (FI); Matti Törmänen, Pudasjärvi (FI)

(73) Assignee: VALMET AUTOMATION OY, Espoo (FI)

( * ) Notice: Subject to any disclaimer, the term of this patent is extended or adjusted under 35 U.S.C. 154(b) by 0 days.

(21) Appl. No.: 15/812,475

(22) Filed: Nov. 14, 2017

(65) Prior Publication Data
US 2018/0164212 A1    Jun. 14, 2018

(30) Foreign Application Priority Data
Dec. 8, 2016  (FI) ..................... 20165938

(51) Int. Cl.
| | | |
|---|---|---|
| G01N 21/53 | (2006.01) | |
| G01N 33/34 | (2006.01) | |
| G01N 21/47 | (2006.01) | |
| G01N 21/85 | (2006.01) | |
| G01N 21/33 | (2006.01) | |

(52) U.S. Cl.
CPC ......... *G01N 21/532* (2013.01); *G01N 21/474* (2013.01); *G01N 21/53* (2013.01); *G01N 21/85* (2013.01); *G01N 33/343* (2013.01); *G01N 21/33* (2013.01); *G01N 2021/475* (2013.01); *G01N 2021/4769* (2013.01); *G01N 2021/8592* (2013.01); *G01N 2201/0826* (2013.01)

(58) Field of Classification Search
CPC ............... G01N 21/532; G01N 33/343; G01N 2201/0826; D21C 3/228
See application file for complete search history.

(56) References Cited

U.S. PATENT DOCUMENTS 4,787,749 A * 11/1988 Ban ................... G01B 11/0625
356/632
4,837,446 A * 6/1989 Renard .................. G01N 15/14
250/458.1

(Continued)

FOREIGN PATENT DOCUMENTS

WO           96/02821 A1    2/1996

OTHER PUBLICATIONS

Moser C. et al., "Toward Industrially Feasible Methods for Following the Process of Manufacturing Cellulose Nanofibers," BioResources, 10(2), pp. 2360-2375, 2015.

(Continued)

*Primary Examiner* — Maurice C Smith
(74) *Attorney, Agent, or Firm* — Oliff PLC

(57) ABSTRACT

A solution for measuring a suspension which contains wood fibres. The consistency of the suspension is changed in a consistency range. Optical radiation is directed at the suspension and the intensity of optical radiation interacted with the suspension is measured at different consistencies in the consistency range. The maximum intensity of the optical radiation is determined within the consistency range. At least one of the following properties of the suspension are determined based on the determined maximum intensity: kappa number, brightness.

15 Claims, 3 Drawing Sheets

(56) References Cited

U.S. PATENT DOCUMENTS

| | | | | |
|---|---|---|---|---|
| 5,220,172 | A * | 6/1993 | Berthold | G01N 21/6408 |
| | | | | 162/49 |
| 5,500,735 | A * | 3/1996 | Bentley | G01N 21/21 |
| | | | | 356/246 |
| 6,118,521 | A * | 9/2000 | Jung | A61B 5/0088 |
| | | | | 250/227.14 |
| 6,475,339 | B1 * | 11/2002 | Chai | D21C 3/228 |
| | | | | 162/49 |
| 6,703,618 | B2 | 3/2004 | Karki et al. | |
| 2001/0017195 | A1 * | 8/2001 | Trung | G01N 21/65 |
| | | | | 162/49 |
| 2006/0196622 | A1 | 9/2006 | Trung et al. | |
| 2007/0045157 | A1 * | 3/2007 | Kajzer | D21B 1/023 |
| | | | | 209/3 |
| 2008/0250848 | A1 * | 10/2008 | Karki | G01N 1/38 |
| | | | | 73/54.01 |
| 2016/0313003 | A1 * | 10/2016 | Masterson | F23M 11/042 |

OTHER PUBLICATIONS

Aug. 16, 2017 Search Report issued in Patent Application No. 20165938.

Mar. 7, 2018 Search Report issued in Austrian Application No. A 51005/2017.

\* cited by examiner ic field, and particularly to optical measurement of kappa number.

METHOD AND MEASUREMENT APPARATUS FOR MEASURING SUSPENSION

TECHNICAL FIELD

The exemplary and non-limiting embodiments of the invention relate generally to measurement of a wood fibre suspension, and particularly to optical measurement of kappa number.

BACKGROUND

The following description of background art may include insights, discoveries, understandings or disclosures, or associations together with disclosures not known to the relevant art prior to the present invention but provided by the invention. Some of such contributions of the invention may be specifically pointed out below, whereas other such contributions of the invention will be apparent from their context.

In paper and pulp manufacturing the purpose is to obtain end product having a good and uniform quality. One way of ensuring the quality is to perform measurements during the manufacturing process. One of the most common and important measurements in the pulp manufacturing is the measurement of the pulp lignin content. The lignin content of a suspension such as pulp is usually denoted with a kappa number. In standard SCAN-C 1:77, which is known in the field of pulp manufacturing, the kappa number is defined as the amount of potassium permanganate solution with a concentration of 20 mmol/l in millilitres which one gram of dry pulp consumes in the conditions defined in the standard.

The lignin content can be measured in laboratory environment with known methods. However, laboratory measurements are not suitable in manufacturing environments where results must be obtained quickly in the different process stages to enable control of the manufacturing process based on the measurements.

Lignin content of suspensions may be measured with online kappa analysers by using optical measurements. These measurements provide results which may be used in process control. Typically the measurements are performed using pulp consistency sweep and two separate optical wavelengths in separate measurement chambers. The use of two wavelengths requires the use of two separate measurement apparatuses, circulating the pulp in the measurement chambers and the use of pressure to remove air bubbles. The measurement system is easily choked and is complicated.

BRIEF DESCRIPTION

An object of the invention is to provide an improved method and an apparatus implementing the method to reduce or avoid the above-mentioned problems.

According to an aspect of the present invention, there is provided a method of measuring a suspension which contains wood fibres, the method comprising: changing consistency of the suspension in a consistency range; directing optical radiation at the suspension and measuring the intensity of optical radiation interacted with the suspension at different consistencies in the consistency range; determining the maximum intensity of the optical radiation within the consistency range; and determining at least one of the following properties of the suspension based on the determined maximum intensity: kappa number, brightness According to an aspect of the present invention, there is provided a measurement apparatus for measuring a suspension which contains wood fibres, the measurement apparatus comprising an optical power source for directing optical radiation at the suspension and at least one optical measurement sensor for measuring optical radiation interacted with the suspension, the measurement apparatus being arranged to change consistency of the suspension in a consistency range; direct optical radiation at the suspension and measure the intensity of optical radiation interacted with the suspension at different consistencies in the consistency range; determine the maximum intensity of the optical radiation within the consistency range; and determine at least one of the following properties of the suspension based on the determined maximum intensity: kappa number, brightness.

Some embodiments of the invention are disclosed in the dependent claims.

BRIEF DESCRIPTION OF THE DRAWINGS

In the following the invention will be described in greater detail by means of preferred embodiments with reference to the accompanying drawings, in which.

DETAILED DESCRIPTION OF SOME EMBODIMENTS

The solution according to the invention is particularly suitable for measuring the kappa number and brightness of a suspension which contains wood fibres, but it is by no means limited to this.

In this application 'optical radiation' means electromagnetic radiation with a wavelength of approximately 40 nm to 1 mm, and 'ultraviolet radiation' means electromagnetic radiation with a wavelength of approximately 40 nm to 400 nm.

In the proposed solution, a suspension which contains wood fibres, is exposed to optical radiation and interaction of the radiation with the suspension is measured while the consistency of the suspension is changed during the measurement process.

Figure 1:
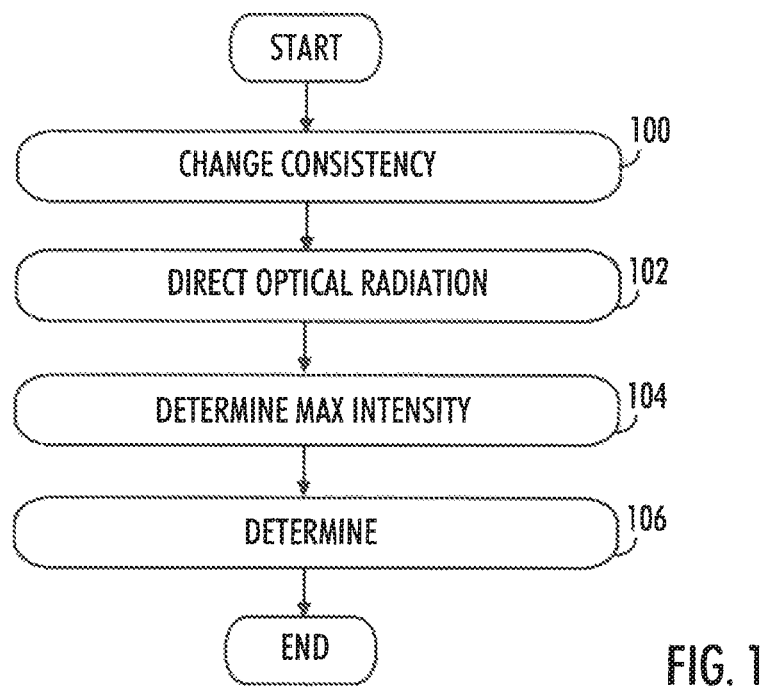
FIG. 1 is a flowchart illustrating an example of an embodiment of the invention.

FIG. 1 is a flowchart illustrating an example of an embodiment of the invention, where suspension which contains wood fibres is measured.

In step 100, consistency of the suspension is changed in a consistency range. In an embodiment, the consistency range extends from an initial consistency to a final consistency.

In step 102, optical radiation is directed at the suspension and the intensity of optical radiation interacted with the suspension is measured at different consistencies in the consistency range. Thus as the consistency of the suspension is changed the measurement is repeated at given intervals. The interval may be a measurement parameter.

In an embodiment, the optical radiation is directed to the suspension using an optical power source; and the intensity of optical radiation interacted with the suspension is measured with one or more optical measurement sensors having a given surface area and distance from the optical power source.

In an embodiment, the given surface area and distance are selected on the basis of the consistency range and desired amount of intensity.

In an embodiment, the optical radiation consists of radiation of a given wavelength.

In step 104, the maximum intensity of the optical radiation within the consistency range is determined.

In step 106, at least one of the following properties of the suspension is determined based on the determined maximum intensity: kappa number, consistency and brightness.

Next, an example of a measurement arrangement of an embodiment will be described with reference to FIG. 2, which shows application of the invention in the pulp and paper industry.

Figure 2:
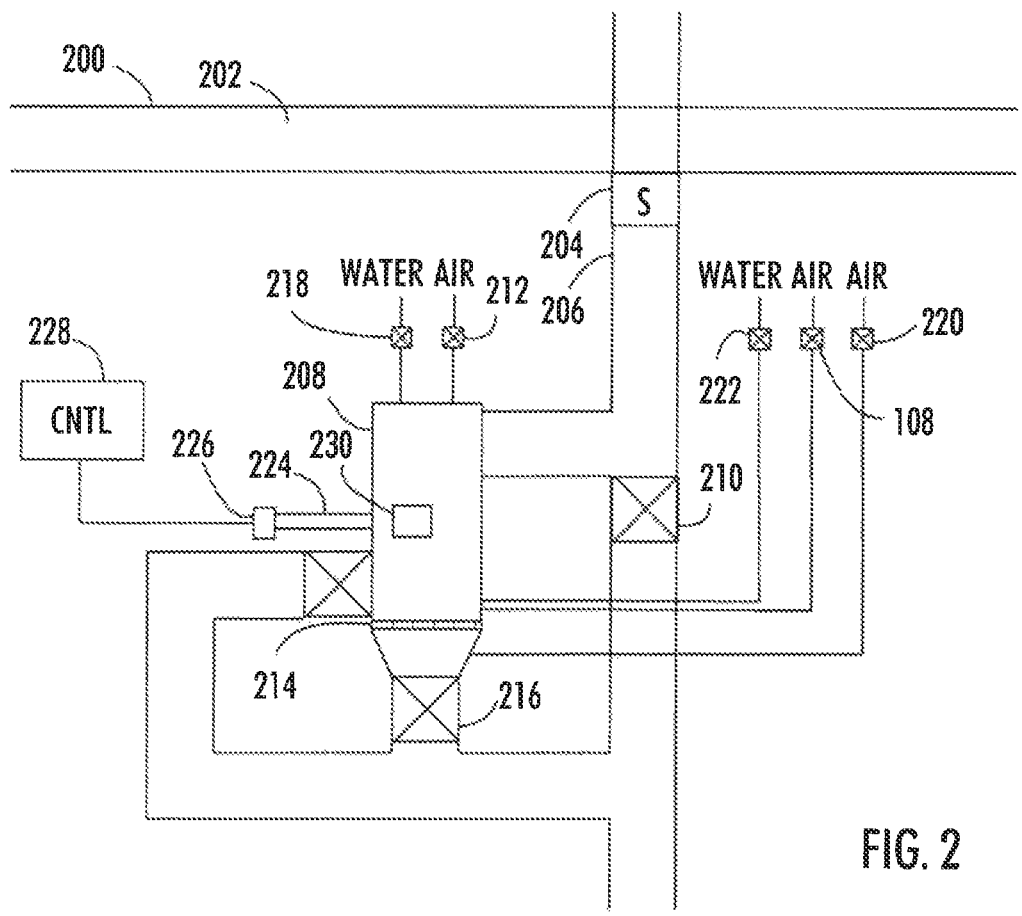
FIG. 2 illustrates an example of a measurement arrangement according to an embodiment.
Figure 3:
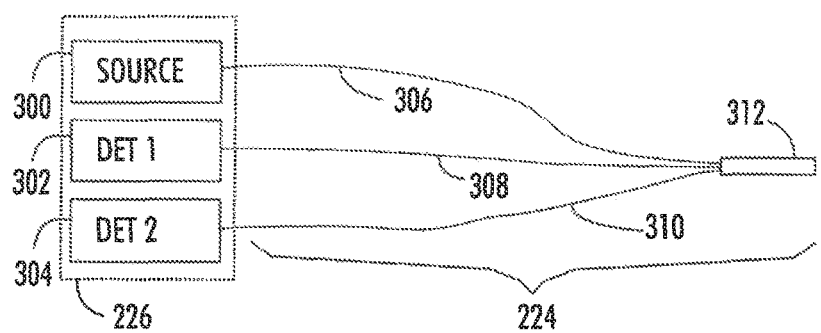
FIG. 3 illustrate an example of measurement arrangement.

FIG. 2 shows a pipe 200 where a suspension 202 containing wood fibres, i.e. wood fibre pulp, is flowing. A sample of the suspension is taken with a sampler 204 from the pipe 200. The sampler 202 may be a solution known per se, e.g. based on a piston and a cylinder. The sample is conveyed using a pipe 206 to a measurement chamber 208, valve 210 being closed.

The suspension in the measurement chamber may be processed prior measurement. For example, liquid may be filtered by using pressured air. Valve 212 may be opened and the air coming through the valve presses the sample against the wire 214 and liquid flows through valve 216.

The sample may be washed using water arid air by opening valves 212 and 218, the waste water flows through the valve 216.

When the sample has been washed measurement process may start by mixing the sample using pressured air through valve 220 and by adding water through valve 222. When sample has been mixed air valve 220 is closed. Water valve 222 is left open. Water comping through the valve changes the consistency of the sample and at the same time mixes the sample. The consistency of the suspension is changed in a consistency range. In an embodiment, the consistency range extends from an initial consistency to a final consistency.

Measuring may be performed during the chancing of the consistency of the sample using measurement arrangement 224, 226 which may be controlled by a measurement controller 228. In an embodiment, the measurement arrangement comprises a source and detector part 226 and optical fibre and measurement head part 226.

FIGS. 3 and 4A to 4C illustrate examples of measurement arrangement 224, 226. In an embodiment, the arrangement comprises an optical power source 300. The kappa number is usually measured in the ultraviolet light, for which reason the optical power source may typically emit at least ultraviolet light. The source 300 may he a Xenon lamp or a LED (light emitting diode), for example. The optical power source direct may be configured to direct optical radiation at the suspension. In an embodiment, the radiation is directed to the suspension using first optical fibre 306. The first optical fibre 306 may be configured to direct the optical radiation at the suspension, the first end of the fibre being connected to the optical light source 300 and the second end of the fibre, located at a measurement head and being inserted in the measurement chamber 208.

In an embodiment, the arrangement further comprises one or more detectors 302, 304 arranged to measure the intensity of optical radiation interacted with the suspension. In an embodiment, each detector is connected to a set of optical fibres 308, 310, the ends of the optical fibres being positioned next to the second end of the first optical fibre 302.

Figures 4A, 4B, 4C:
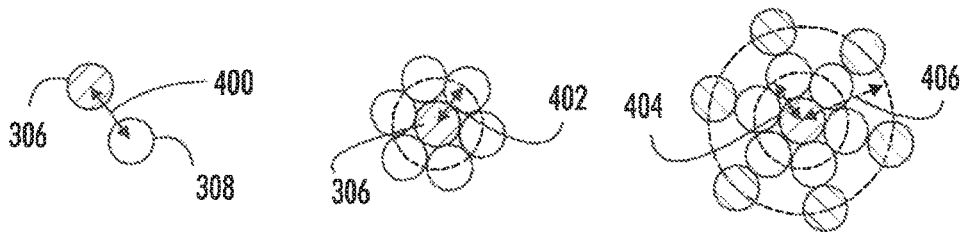
FIGS. 4A, 4B and 4C illustrate examples of measurement arrangement.

FIG. 4A to 4C illustrate examples of the fibre arrangement in the measurement head 312 which may be inserted into the measurement chamber 208.

FIG. 4A illustrates an embodiment, where the measurement arrangement comprises the optical power source 300 connected to first optical fibre 308 and detector 302 connected to optical fibre 308. At the measurement head the first optical fibre 306 and the optical fibre 308 are located side by side with a given distance 400 from each other.

FIG. 4B illustrates another embodiment, where the measurement arrangement comprises the optical power source 300 connected to first optical fibre 308 and detector 302 connected to a set of optical fibres 308. At the measurement head the ends of the optical fibres 308 are positioned next to the end of the first optical fibre 306 at a same given distance 402 from the first optical fibre.

FIG. 4C illustrates another embodiment, where the measurement arrangement comprises the optical power source 300 connected to first optical fibre 308 and detectors 302, 304 connected to a set of optical fibres 308, 310. At the measurement head the ends of the optical fibres 308 are positioned next to the end of the first optical fibre 306 at a same given distance 404 from the first optical fibre and the ends of the optical fibres 310 are positioned next to the end of the first optical fibre 306 at a same given distance 406 from the first optical fibre.

In an embodiment, the measurement chamber 208 comprises a window 230 in the wall of the measurement chamber. The optical power source 300 or the first optical fibre 306 connected to the source may be placed outside the measurement chamber behind the window for directing optical radiation at the suspension.

Likewise one or more detectors 302, 304 or optical fibres 308, 310 connected to the detectors may be placed outside the measurement chamber behind the window 230 in the measurement chamber wall.

The use of optical fibres described above is merely an example. The measurement may be realised also without optical fibres. In an embodiment, the optical radiation is led to the measurement chamber using a radiation conductor such as a lens, a wave guide or any suitable medium. For example, the optical source and detectors may be placed behind the window 230 without the use of any optical fibres.

Figure 5:
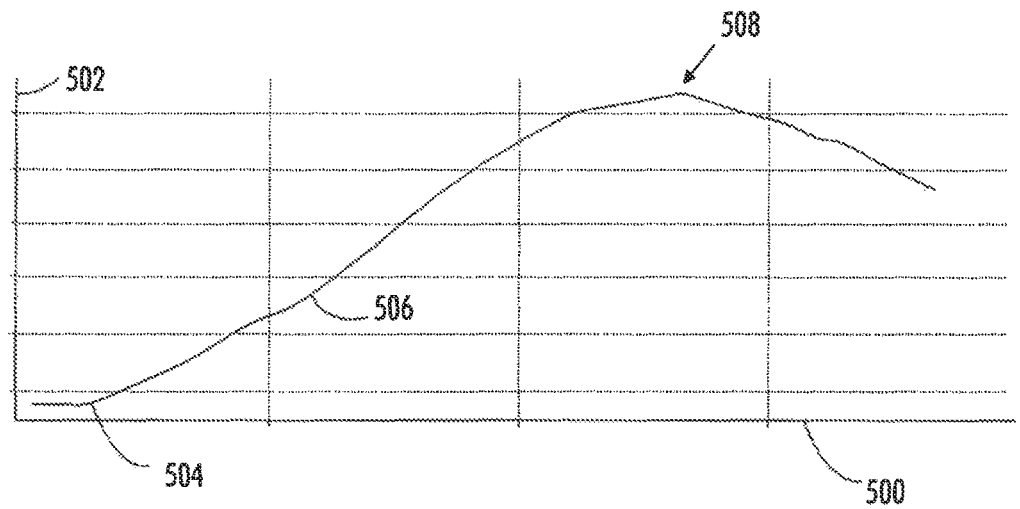
FIG. 5 illustrates an example of measurement results.

FIG. 5 illustrates an example of measurement results when the intensity of optical radiation interacted with suspension at different consistencies is measured using above described measurement arrangement. FIG. 5 is a graph where time is on the x-axis 500 and measured intensity is on the y-axis 502. The consistency of the suspension sample is changed as a function of time. Typically, in the beginning the suspension is large and as more water is mixed with the sample the suspension gets lower.

As optical radiation from the optical power source is directed to the sample of the suspension, part of the radiation scatters from the wood fibres to the detector, part scatters elsewhere and part absorbs in lignin. The consistency of the sample of the suspension is changed during measurement process. In the beginning when the consistency is larger, a small amount 504 of radiation is detected by the detector. When the consistency is smaller due to the water mixed in the sample, the amount 506 of radiation detected by the detector increases. At some point, when the consistency gets smaller, the amount of radiation detected by the detectors gets smaller. The measurement arrangement may be configured to detect the maximum value 508 of the intensity detected by the detector. Based on the determined maximum intensity, at least one of the following properties of the suspension may be determined: kappa number, brightness.

The consistency with which the maximum intensity is reached depends on absorption. The greater the absorption the smaller the consistency with which the maximum intensity occurs.

In an embodiment, the initial consistency of the consistency range measurement depends on the properties of the suspension. The measurement continues until the maximum intensity has been detected and is terminated when the measured intensity is getting smaller after the maximum value.

In an embodiment, the measurement arrangement is calibrated to function correctly by performing calibration measurements. These measurements may be performed using a normalizing reference plate placed in front of the measurement arrangement. In an embodiment, the calibration is performed using reference pulp. Calibration is necessary before the measurement apparatus is actually used and needs to be performed from time to time because the route of optical radiation, for example, may change or the detector responses may change in the course of time. The reference pulp is wood fibre pulp whose properties have been measured in the laboratory and stabilized with respect to time. There is reference pulp commercially available for calibration of the measurement apparatus, e.g. Paprican standard reference pulp 5-96 from a Canadian manufacturer.

In an embodiment, the surface areas and numerical apertures of the optical source and the detectors are selected on the basis of the consistency range of the suspension and desired amount of intensity.

In an embodiment, the distances 400, 402, 404, 406 and the surface area of the cross sections and numerical apertures of optical for fibres or sets of optical fibres 306, 308 and 310 are selected on the basis of the consistency range of the suspension and desired amount of intensity.

The distances 400, 402, 404, 406 and the surface area of the cross sections of optical for fibres or sets of optical fibres 306, 308 are denoted in following as measurement geometry. Measurement geometry relates to the consistency range. When measurements are made, the consistency of the suspension must be such that sample processing (washing of sample and changing the consistency) are possible. If the consistency of the suspension is too large the sample processing may not succeed. On the other hand, if the consistency is too low dynamics of the measurement suffers. Also available intensity of light from the optical light source has an effect on the measurements. When kappa number is measured, the large the kappa is the more the lignin in the sample absorbs light.

In an embodiment, the purpose is to detect the maximum intensity of the optical radiation interacted with the suspension within the consistency range. The consistency at which the maximum intensity is reached may depend on following issues:

The distance 400, 402, 404, 406 between the optical power source and the measurement point, i.e the distance between the end of the first optical fibre 306 and the ends of other optical fibres 306, 308. The larger the distance the smaller is the consistency when maximum intensity occurs.

The surface areas of the optical power source and measurement points. The larger the surface areas the smaller is the consistency when maximum intensity occurs.

The kappa number of the sample. The larger the kappa number the smaller is the consistency when maximum intensity occurs.

Wavelength of the radiation outputted by the optical power source. Absorption of the radiation in the suspension depends on the wavelength. The larger the absorption the smaller is the consistency when maximum intensity occurs.

Particle size of the sample of the suspension. The smaller the particles, the smaller is the consistency when maximum intensity occurs.

Thus in an embodiment, measurement parameters may comprise the measurement geometry, the wavelength of the optical radiation and the consistency range used in the measurements. For example, for high kappa values a different wavelength may be used compared to low kappa values. In an embodiment, the wavelength is ultra-violet range. Further, the consistency range may depend on the properties of the suspension. For example, when measuring pine suspension consistency range may be 0.3-0.1% and when measuring birch suspension consistency range may be 0.4-0.2%, These numerical values are only non-limiting examples.

Typical values for optical fibre diameters are around few hundred μm, but also other values may be used depending on the property to be measured, In general, the above discussion applies also when optical fibres are not used but the optical source and detectors are connected to the measurement chamber using some other suitable medium.

Figure 6:
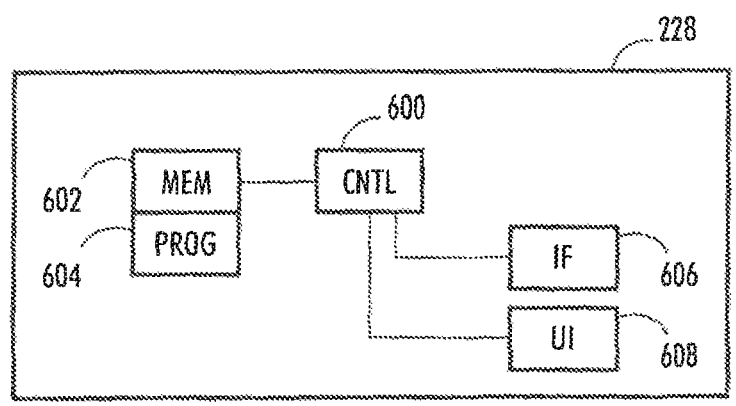
FIG. 6 illustrates an example of an apparatus configured to act as a measurement controller.

FIG. 6 illustrates an embodiment. The figure illustrates a simplified example of an apparatus configured to act as a measurement controller 228, It should be understood that the apparatus is depicted herein as an example illustrating some embodiments. It is apparent to a person skilled in the art that the apparatus may also comprise other functions and/or structures and not all described functions and structures are required. Although the apparatus has been depicted as one entity, different modules and memory may be implemented in one or more physical or logical entities, The apparatus 228 of the example includes a control circuitry 600 configured to control at least part of the operation of the apparatus.

The apparatus may comprise a memory 602 for storing data. Furthermore the memory may store software 604 executable by the control circuitry 240. The memory may be integrated in the control circuitry.

The apparatus may further comprise an interface circuitry 606 configured to connect the apparatus to other devices. The interface may provide a wired or wireless connection. The interface may be connect the apparatus to the measurement arrangement 224, 226. In an embodiment, the apparatus may be connected to an automatic process control computer used in the manufacture of pulp.

The apparatus may further comprise user interface 608 such as a display, a keyboard and a mouse, for example. In an embodiment, the apparatus does not comprise user interface but is connected to other devices providing access to the apparatus.

In some embodiments, the apparatus may be realised with a mini- or microcomputer, a personal computer or a laptop or any suitable computing device.

The proposed solution for measuring suspension has many advantages over prior art solutions. There is no need for a separate consistency measurement which reduces measuring inaccuracy. Compared to prior art measuring arrangements the proposed arrangement is simpler to realise. There is no need to circulate sample during measurements, and the number of pumps and valves may be reduced. There is no separate washing chamber as washing and measurement may be performed in the same chamber. Further, there is no need for pressured measurement chamber. Based on the structure of the arrangement it is possible to perform calibration using a normalizing reference plate.

In an embodiment, brightness and consistency measurements may be performed in the same measurement chamber using different measuring geometry. For example, in the solution of FIG. 4C one detector may measure kappa number and other brightness.

It will be obvious to a person skilled in the art that, as the technology advances, the inventive concept can be implemented in various ways. The invention and its embodiments are not limited to the examples described above but may vary within the scope of the claims.

The invention claimed is:

1. A method of measuring a suspension which contains wood fibers, the method comprising:
   changing a consistency of the suspension in a consistency range;
   directing optical radiation at the suspension and measuring an intensity of optical radiation having interacted with the suspension at different consistencies in the consistency range;
   determining a maximum of the intensity of the optical radiation within the consistency range; and
   determining at least one of kappa number or brightness of the suspension based on the determined maximum of the intensity.

2. The method as claimed in claim 1, further comprising:
   directing the optical radiation to the suspension using an optical power source; and
   measuring the intensity of optical radiation having interacted with the suspension with one or more optical measurement sensors having a given surface area, numerical aperture and distance from the optical power source.

3. The method as claimed in claim 2, further comprising:
   selecting the given surface area, numerical aperture and distance based on the consistency range and a desired amount of intensity.

4. The method as claimed in claim 1, further comprising: measuring the kappa number using ultraviolet radiation.

5. The method as claimed in claim 1, further comprising:
   changing the consistency of the suspension so that the consistency continuously goes through all consistencies in the consistency range.

6. The method as claimed in claim 1, further comprising: taking a sample of the suspension to an unpressurised measurement chamber.

7. The method as claimed in claim 1, further comprising:
   directing the optical radiation at the suspension using a first optical fiber having a given diameter and numerical aperture; and
   measuring the intensity of optical radiation having interacted with the suspension with a detector connected to a set of optical fibers, each optical fiber having a given diameter, and ends of the optical fibers being positioned next to an end of the first optical fiber at a same given distance from the first optical fiber.

8. The method as claimed in claim 6, further comprising:
   directing the optical radiation at the suspension using a light source placed outside the measurement chamber behind a window in a measurement chamber wall; and
   measuring the intensity of optical radiation having interacted with the suspension with a detector placed outside the measurement chamber behind the window in the measurement chamber, the detector having a given diameter, and located a given distance from the light source.

9. A measurement apparatus for measuring a suspension which contains wood fibers, the measurement apparatus comprising:
   an optical power source for directing optical radiation at the suspension in a measurement chamber;
   at least one optical measurement sensor for measuring optical radiation having interacted with the suspension; and
   control circuitry configured to cause the measurement apparatus to:
      change a consistency of the suspension in a consistency range by controlling a valve connected to a water supply;
      direct optical radiation at the suspension and measure an intensity of optical radiation having interacted with the suspension at different consistencies in the consistency range;
      determine a maximum of the intensity of the optical radiation within the consistency range; and
      determine at least one of kappa number or brightness of the suspension based on the determined maximum of the intensity.

10. The apparatus as claimed in claim 9, wherein:
    at least one measurement sensor has a given surface area, numerical aperture and distance from the optical power source, the given surface area and distance being based on the consistency range and a desired amount of intensity.

11. The apparatus as claimed in claim 9, further configured to measure the kappa number using ultraviolet radiation.

12. The apparatus as claimed in claim 9, further configured to change the consistency of the suspension so that the consistency continuously goes through all consistencies in the consistency range.

13. The apparatus as claimed in claim 9, wherein the measurement chamber is unpressurized.

14. The apparatus as claimed claim 9, further comprising:
    a first optical fiber configured to direct the optical radiation at the suspension, a first end of the fiber being connected to the optical power source and a second end of the fiber being in the measurement chamber; and
    one or more detectors for measuring the intensity of optical radiation having interacted with the suspension, each detector being connected to a set of optical fibers, each optical fiber having a given diameter, and ends of the optical fibers being positioned next to the second end of the first optical fiber at a same given distance from the first optical fiber, the given diameter and distance being based on the consistency range and desired amount of intensity.

15. The apparatus as claimed in claim 9, further comprising
    a window in a measurement chamber wall, the optical power source being placed outside the measurement chamber behind the window in the wall for directing the optical radiation at the suspension; and
    one or more detectors for measuring the intensity of optical radiation having interacted with the suspension, the detectors being placed outside the measurement chamber behind the window in the measurement chamber wall, each detector having a given diameter, and located a given distance from the optical power source, the given diameter and distance being based on the consistency range and a desired amount of intensity.

\* \* \* \* \*